United States Patent [19]

Hoeffkes et al.

[11] Patent Number: 4,698,065
[45] Date of Patent: Oct. 6, 1987

[54] LIQUID OXIDATION HAIR DYE WITH PHASE STABILIZER

[75] Inventors: Horst Hoeffkes, Duesseldorf-Hellerhof; Dieter Schrader, Duesseldorf, both of Fed. Rep. of Germany

[73] Assignee: Henkel Kommanditgesellschaft auf Aktien, Duesseldorf, Fed. Rep. of Germany

[21] Appl. No.: 816,919

[22] Filed: Jan. 8, 1986

[30] Foreign Application Priority Data

Jan. 12, 1985 [DE] Fed. Rep. of Germany ....... 3500877

[51] Int. Cl.$^4$ .............................................. A61K 7/13
[52] U.S. Cl. .......................................... 8/406; 8/408; 8/416; 8/421; 252/174.19; 252/548; 424/70
[58] Field of Search .................... 524/243; 8/405, 406, 8/636, 408, 416, 421; 424/70; 252/529, 548, 174.19

[56] References Cited

U.S. PATENT DOCUMENTS

| | | | |
|---|---|---|---|
| 2,411,215 | 11/1946 | Kise et al. | 260/342.4 |
| 3,288,770 | 11/1966 | Butler | 526/204 |
| 3,472,840 | 10/1969 | Stone et al. | 536/43 |
| 3,579,453 | 5/1971 | Dupre et al. | 252/174.19 |
| 4,157,388 | 6/1979 | Christiansen et al. | 424/70 |
| 4,233,164 | 11/1980 | Davis | 252/8.75 |
| 4,381,919 | 5/1983 | Jacquet et al. | 8/406 |
| 4,486,338 | 12/1984 | Ootani et al. | 252/174.19 |
| 4,555,246 | 11/1985 | Grollier et al. | 8/406 |

FOREIGN PATENT DOCUMENTS

552268 6/1932 Fed. Rep. of Germany.
1603321 11/1981 United Kingdom.

OTHER PUBLICATIONS

"Alphabetical List of New Products Developed Since Nov. 1964", *American Dyestuff Reporter*, Dec. 6, 1965, p. 61.
"Industrial Utilization of $C_{21}$ Dicarboxylic Acid" Journal of the American Oil Chemists' Society, vol. 52 (1975), pp. 219-224, Ward et al.
"Dimer Acids", Journal of the American Oil Chemists' Society, vol. 39 (1962), pp. 534 et seq. J. C. Cowan.

*Primary Examiner*—Paul Lieberman
*Assistant Examiner*—L. Skaling
*Attorney, Agent, or Firm*—Ernest G. Szoke; Henry E. Millson, Jr.; Mark A. Greenfield

[57] ABSTRACT

Stabilized liquid preparations for oxidation hair dyes are provided. The oxidation hair dyes comprise oxidation hair dye precursors and an aqueous or aqueous-alcoholic carrier, containing (A) from 5 to 20% by weight of fatty acid water-soluble soap and (B) from 0.5 to 10% by weight of a water-soluble cationic polymer. The oxidation hair dyes (containing a soap and cationic polymer which tend towards inhomogeneity) are stabilized by the addition of from 5 to 30% by weight of a compound selected from the group consisting of: (C) aliphatic or alicyclic $C_9$-$C_{44}$ dicarboxylic acid water-soluble salts; and (D) amines corresponding to the following general formula

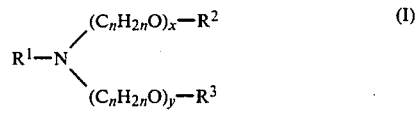

28 Claims, No Drawings

LIQUID OXIDATION HAIR DYE WITH PHASE STABILIZER

BACKGROUND OF THE INVENTION

1. Field of the Invention

The present invention relates to liquid preparations containing oxidation hair dyes and more particularly relates to a means and method of stabilizing liquid preparations containing oxidation hair dyes.

2. Description of Related Art

Liquid oxidation hair dye preparations contain hair dye precursors and a cosmetic carrier suitable for application to hair. The carriers preferably used are either cream-like emulsions of the water-in-oil type or aqueous or aqueous-alcoholic solutions of soaps. Oxidation hair dye bases in the form of liquid, aqueous or aqueous-alcoholic soap solutions have the desirable property of forming a thickly liquid to gel-like, ready-to-use hair dyeing preparation after adding an aqueous oxidizing developer solution.

It is also known that water-soluble cationic polymers may be added to hair dyeing preparations to condition and improve the cosmetic properties of the hair.

However, difficulties are involved in producing liquid preparations of oxidation hair dyes containing soaps and cationic polymers because these preparations tend to be inhomogeneous and, in some cases, can become cloudy, separate and/or form a sediment, resulting in the gradual loss of their hair-conditioning properties due to the interaction of the cationic polymer with the soap. On the other hand, oxidation hair dye preparations based on liquid, aqueous or aqueous-alcoholic soap solutions are very desirable because, after addition of the aqueous oxidizing developer, they form thickly liquid to gel-like dye preparations which can easily adhere to the hair after application. Accordingly, there has been a need in the art for a suitable formulation enabling soaps and cationic polymers to be incorporated in hair dye bases of this type.

DESCRIPTION OF THE INVENTION

It has been found that liquid preparations of oxidation hair dyes having a hair dye precursor and an aqueous or aqueous-alcoholic carrier which contain (A) from 5 to 20% by weight of $C_{12}$–$C_{22}$ fatty acids in the form of a water-soluble soap and (B) from about 0.5 to 10% by weight of a water-soluble cationic polymer having a molecular weight of from about 1000 to 3,000,000 remain homogeneous and stable in storage when they contain from about 5 to 30% by weight of one or more compounds selected from the group consisting of:

(C) aliphatic or alicyclic $C_9$–$C_{44}$ dicarboxylic acids in the form of water-soluble salts; and (D) amines corresponding to the following general formula

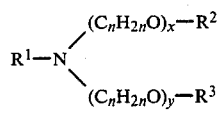

in which $R^1$ is a $C_8$–$C_{22}$ alkyl group, $R^2$ and $R^3$ independently of one another represent hydrogen or an acyl group of the formula $R^4$—COO— where $R^4$ is a $C_1$–$C_{21}$ alkyl group or alkenyl group, n is 2 or 3 and x and y are 0 or a number of from 1 to 5, the sum of x+y being in the range of from 2 to 6.

Unstable aqueous systems of soap and cationic polymers are surprisingly stabilized by the addition of a dicarboxylic acid and/or amine corresponding to the above formula and the conditioning properties of the cationic polymer remain intact.

Preferred fatty acids for forming the soaps (A) are those which are liquid at 20° C. Examples include unsaturated linear fatty acids, such as oleic acid, linoleic acid, palmitoleic acid, erucic acid or liquid mixtures thereof. The mixtures may also include relatively small amounts of saturated linear fatty acids containing from 12 to 22 carbon atoms. Other preferred liquid fatty acids include branched fatty acids, for example 2-hexyl decanoic acid, 2-octyl dodecanoic acid and isostearic acid.

Alkali hydroxides, alkali carbonates, ammonia and also mono-, di- and trialkanol-amines containing from 2 to 4 carbon atoms in the alkanol group are suitable for converting the fatty acids into the water-soluble soap.

Oleic acid soaps, in the form of the ammonium, mono-, di- or triethanolammonium soap, are especially preferred.

Suitable water-soluble cationic polymers (B) have a molecular weight in the range from about 1000 to 3,000,000 and contain free or alkyl-substituted amino groups or quaternary ammonium groups in the polymer chain. The cationic polymers may also have primary, secondary or tertiary amino groups or quaternary ammonium groups attached to the polymer chain, either directly or by intermediate members. These amino groups or quaternary ammonium groups may also be members of 5- or 6-membered ring systems, for example the morpholine, piperidine, piperazine or imidazole ring systems. Numerous examples of water-soluble cationic polymers of this type are described in detail, for example, in Great Britian Pat. No. 1 603 321. In addition, many other water-soluble cationic polymers are known.

Especially preferred are water-soluble homopolymers or copolymers (B1) containing units corresponding to the following general formula

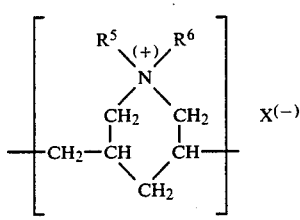

in which $R^5$ and $R^6$ represent hydrogen or $C_1$–$C_4$ alkyl groups or $C_2$–$C_4$ hydroxyalkyl groups and $X^{(-)}$ is a chloride, bromide, hydrogen sulfate, methosulfate, phosphate or acetate anion. Examples of cationic polymers of this type include, for example, commercial products sold under the trademark Merquat 100 and Merquat 550 by Merck & Co., Inc., Rahway, N.J. (Quaternium 41). Methods of producing these polymers are known, for example, from U.S. Pat. No. 3,288,770.

Other preferred cationic polymers include cellulose ethers (B2) having anhydroglucose units containing from 1 to 3 substituents containing quaternary ammonium groups attached by ether linkages. Polymers of this type are known, for example, from U.S. Pat. No. 3,472,840. One example having this structure is a product sold under the trademark Polymer JR 400 by Union Carbide Corp., Danbury, Conn.

Other preferred cationic polymers include the quaternary polymeric urea derivatives (B3) disclosed in U.S. Pat. No. 4,157,388. One cationic polymer of this type is sold under the trademark Mirapol A15 by Miranol Chemical Co., Inc., Irvington, N.J. and comprises structural units corresponding to the following general formula

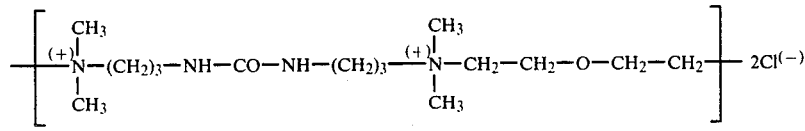

and has an average degree of polymerization of approximately 6.

Suitable dicarboxylic acids (C) are linear or branched, saturated or unsaturated dicarboxylic acids containing from 9 to 44 carbon atoms, for example, azelaic acid, sebacic acid, brassylic acid, docosanedioic acid, and 2-alkyl and 2-alkenyl succinic acids containing from 5 to 40 carbon atoms in the alkyl or alkenyl group. The alkyl and alkenyl succinic acids are known compounds. The production of the alkenyl succinic acid anhydrides from maleic acid anhydride and monoolefins is known, for example, from U.S. Pat. No. 2,411,215. The alkenyl succinic acid anhydrides may readily be converted into the corresponding alkyl succinic acid anhydrides by hydrogenation of the double bond.

Other suitable dicarboxylic acids are the so-called dimer acids which may be obtained by thermal dimerization of mono- and poly-unsaturated fatty acids (for example mixtures of oleic acid and linoleic acid) in a Diels-Alder type addition reaction. These dimer acids and their commercial production are described in detail, for example, in the J. Am. Oil Chem. Soc. 39 (1962), pages 534 et seq. The mono-unsaturated dimer acids initially formed may readily be converted into corresponding saturated dicarboxylic acids by catalytic hydrogenation of the double bond. Dimer acids such as these are sold commercially by Emery Industries, Inc., Cincinnati, Ohio under the trademark Empol 1010.

Other suitable dicarboxylic acids comprise the -ene adducts of mono-unsaturated carboxylic acids, such as acrylic or methacrylic acid, with unsaturated fatty acids, such as undecylenic acid, oleic acid, palmitoleic acid, linoleic acid or erucic acid. An especially preferred branched dicarboxylic acid of this type is 5(6)-carboxy-4-hexyl-2-cyclohexane-1-octanoic acid. This dicarboxylic acid, is described in detail in J. Am. Oil Chem. Soc. 52 (1975), pages 219–224 and is sold by Westvaco Corp., Covington, Va., under the trademark Diacid 1550.

Aliphatic and/or alicyclic dicarboxylic acids used in accordance with the present invention are present in the hair dye preparations in the form of their water-soluble salts, generally lithium, sodium, potassium, ammonium, mono-, di- and triethanolammonium and/or isopropanolammonium salts. However, it is also possible to use salts of these dicarboxylic acids with other inorganic or organic bases, provided that 5 to 30% by weight of the aqueous or aqueous-alcoholic hair dye preparations of the present invention is in the form of the dissolved dicarboxylic acid salt.

Amines (D) corresponding to the following general formula

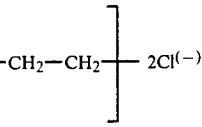 (I)

in which $R^1$, $R^2$, $R^3$, n, x and y are as defined above, may be synthesized from primary $C_8$–$C_{22}$ fatty amines by the addition of (x+y) moles of ethylene oxide or propylene oxide, for example, in accordance with the teachings of German Pat. No. 552,268. Alkoxylated fatty amines of general formula I, in which $R^2$ and $R^3$ represent hydrogen, are initially obtained by the addition of ethylene oxide or propylene oxide onto fatty amines. These products may be converted into the compounds of general formula I, in which $R^2$ and $R^3$ represent an acyl group of the formula $R^4$—COO—, by esterification with carboxylic acids corresponding to the general formula $R^4$—COOH, in which $R^4$ is a $C_1$–$C_{21}$ alkyl group, or with methyl esters or acid chlorides of these carboxylic acids. Products corresponding to general formula I are sold commercially. For example, an adduct of 3 moles of ethylene oxide with a $C_{12}$–$C_{14}$ fatty alcohol is sold by Jos. H. Lowenstein & Sons, Brooklyn, NY under the trademark Lowenol C-243. A bis-d(2-hydroxy-ethyl)-soya alkylamine dioleate is also sold under the following trademarks: Araphen, Genamin (sold by Farbwerke Hoechst, Frankfort, Germany), Marlazin, and Lutensol (sold by BASF AG, Ludwigshafen, Germany).

In addition to the carrier components mentioned above, the hair dye preparations of the present invention also contain oxidation hair dye precursors. The oxidation hair dye precursors may comprise known dye bases, developer compounds, modifiers and/or coupler compounds. The oxidation dyes are formed by oxidative coupling of one or more developer compounds or by oxidative coupling of a developer compound wit one or more coupler compounds in the presence of an oxidizing agent. The developer compounds normally used are primary aromatic amines containing another free or substituted hydroxy or amino group in the para or ortho position, diaminopyridine derivatives, phenols, naphthols, resorcinol derivatives or pyrazolones. The hair dye preparations of the present invention may contain the oxidation hair dye precursors in a quantity of from 0.05 to 5.0% by weight and preferably in a quantity of from 0.2 to 2.0% by weight.

The hair dye preparations of the present invention may optionally contain synthetic anionic, nonionic, ampholytic or zwitter-ionic surfactants in quantities of up to 20% by weight. Suitable compounds include, for example, linear alkyl sulfates containing from 12 to 18 carbon atoms in the alkyl group, alkyl polyglycol ether sulfates containing from 12 to 16 carbon atoms in the alkyl group and from 1 to 6 glycol ether groups in the molecule, fatty alcohol polyglycol ethers obtained by the addition of 6 to 20 moles of ethylene oxide onto $C_{10}-C_{18}$ fatty alcohols, adducts of 6 to 20 moles of ethylene oxide with nonyl or dodecyl phenol, fatty alkyl dimethylamine oxides, fatty acid mono- or diethanolamides, N-fatty alkyl dimethyl glycine, N-fatty alkyl aminopropionic acid as well as other known surfactants.

In addition, the hair dye preparations of the present invention may contain from 0 to 20% by weight of $C_{12}-C_{22}$ fatty alcohols, for example coconut oil fatty alcohol, lauryl alcohol, myristyl alcohol, cetyl alcohol, oleyl alcohol or stearyl alcohol in emulsified form. Also suitable are synthetic branched alcohols, for example, 2-octyl dodecanol, 2-hexyl decanol, isostearyl alcohol and isohexadecyl alcohol.

The hair dye preparations according to the invention preferably contain lower $C_1-C_4$ alcohols and/or lower $C_2-C_6$ glycols, for example, ethanol, isopropanol, n-propanol, ethylene glycol, 1,2-propylene glycol, methyl glycol, ethyl glycol, butyl glycol, diethylene glycol, dipropylene glycol or hexylene glycol. These lower alcohols or glycols are preferably present in the preparations in a total quantity of from 10 to 30% by weight. The addition of these lower alcohols and/or polyols keeps the preparations free flowing and readily processible at 20° C. A thickly liquid to gel-like, ready-to-use hair dye is then formed by the addition of a substantially equal quantity of water or aqueous hydrogen peroxide developer solution immediately before application to the hair.

In addition to the components mentioned above, the hair dye preparations according to the invention may also contain known stabilizing additives used in oxidation hair dye bases of this type. These additives include complexing agents, for example, ethylene diamine tetraacetic acid, nitrilotriacetic acid, 1-hydroxy-ethane-1,1-diphosphonic acid or other organodiphosphonic acids in the form of their alkali salts; antioxidants such as, for example, sodium sulfite, sodium bisulfite, hydroquinone or salts of thioglycolic acid or ascorbic acid; buffer salts such as, for example, ammonium sulfate, ammonium carbonate, ammonium citrate and also ammonia or alkanolamine to adjust the pH to within 8 to 10.

Although certain embodiments of the invention have been selected for description in the examples hereinafter, it will be appreciated by those skilled in the art that these examples are merely illustrative of, but do not in any way limit, the scope of the present invention which is defined in the appended claims.

EXAMPLES

The following materials (numbered (1) through (6)) were used in the Examples and had the following compositions:

| (1) Dye solution: | |
| --- | --- |
| resorcinol | 0.0825 g |
| p-tolylene diamine | 0.2607 g |
| p-aminophenol | 0.0662 g |
| 4-chlororesorcinol | 0.0545 g |
| 1,3-bis-(2,4-diaminophenoxyl)-propane tetrahydrochloride | 0.0038 g |
| 2,4-dichloro-3-aminophenol | 0.0470 g |
| ammonia (conc., approx. 25% by weight in water) | 0.4 g |
| water was added to achieve a total of 7.0 g of dye solution | |
| (2) Stabilizer solution: | |
| ethylene diamine tetraacetic acid, Na salt | 0.2 g |
| (NH$_4$)SO$_4$ | 1.0 g |
| Na$_2$SO$_3$ | 0.3 g |

| -continued | |
| --- | --- |
| Na ascorbate | 0.2 g |
| ammonia (conc., approx. 25% by weight in water) | 0.1 g |
| water was added to achieve a total of 8.0 g of dye solution | |
| (3) Mirapol A-15: | poly[N—[3-(dimethyl(ammonio)propyl]-N'—[3[(ethylene-oxyethylene-dimethyl-ammonio)-propyl]-urea dichloride] |
| (4) Lowenol C 243: | adduct of 3 moles of ethylene oxide with cocoalkylamine |
| (5) Lowenol S216X: | bis(2hydroxyethyl)soya alkylamine dioleate |
| (6) Polymer JR 400: | cationic cellulose derivative |

An oxidation hair dye preparation was prepared having the following components:

Example 1

| Ammonium oleate (85% by weight in water) | 7.5 g |
| --- | --- |
| $C_{12}-C_{14}$ fatty alcohol-2EO-sulfate, Na salt (28% by weight in water, Texapon N25 sold by Henkel KGaA, Dusseldorf | 3.5 g |
| Nonylphenol polyglycol ether (9 moles ethylene oxide) | 12.0 g |
| Lauryl alcohol | 6.5 g |
| 1,2-propylene glycol | 8.0 g |
| Water | 15.0 g |
| Stabilizer solution No. (2) | 8.0 g |
| Dye solution No. (1) | 7.0 g |
| Mirapol A15 No. (3) | 3.0 g |
| Westvaco Diacid 1550 | 10.0 g |
| Perfume oil | 0.2 g |
| Ammonia (conc., approx. 25% by weight in water) | 5.0 g |
| Isopropanol | 10.0 g |
| Water - added to achieve a total of 100 g of solution | |

The ammonium oleate, fatty alcohol ether sulfate, nonyl phenol polyglycol ether, lauryl alcohol and 1,2-propylene glycol were heated with 15 g of water to a temperature of 35° C. Then the stabilizer solution, the dye solution, the mixture of Mirapol A15 and Westvaco Diacid 1550 and the perfume were added, in the order stated. The pH was then adjusted to 10 with ammonia solution. Finally, the isopropanol and remaining water were added.

Example 2

A second oxidation hair dye preparation was synthesized having the following components:

| Propylene glycol | 8.6 g |
| --- | --- |
| Lowenol C243 No. (4) | 8.0 g |
| Isopropanol | 12.5 g |
| Oleic acid | 8.6 g |
| Lowenol S-216-X No. (5) | 21.6 g |
| Monoethanolamine | 8.0 g |
| Stabilizer solution No. (2) | 8.0 g |
| Dye solution No. (1) | 7.0 g |
| Polymer JR 400 No. (6) | 2.0 g |
| Water | 23.0 g |
| Perfume oil | 0.2 g |
| Water - added to achieve a total of 100 g of solution | |

The propylene glycol and Lowenol C243 were heated together to a temperature of 70° C. Then the isopropanol was added and the mixture stirred at 70° C. until a clear solution had formed. The oleic acid, Lowenol S216X and monoethanolamine were then added. After cooling, the stabilizer solution, the dye solution, a solution of Polymer JR 400 in 23 g of water, the perfume oil and the remaining water were added in the order stated, with stirring. The pH was adjusted to 10.0 with monoethanolamine.

The hair dye preparations synthesized in Examples 1 and 2 were low viscosity liquids. Just before application, the hair dye preparations were mixed at a 1:1 weight ratio with a 6 wt% hydrogen peroxide solution. Thickly liquid to gel-like dyes were obtained.

Although the present invention has been described in terms of a number of specific examples and embodiments thereof, it will be appreciated by those skilled in the art that a wide variety of equivalents may be substituted for the specific parts and steps of operation described herein, all without departing from the spirit and scope of the present invention, as defined in the appended claims.

We claim:

1. A homogeneously stabilized liquid oxidation hair dye preparation comprising:
(A) a hair dye-effective amount of a hair dye precursor;
(B) an aqueous or aqueous-alcoholic carrier;
(C) about 5 to 20% by weight of a fatty acid water-soluble soap;
(D) a conditioning-effective amount of at least one water-soluble cationic polymer; and
(E) a stabilizer-effective amount of at least one water-soluble compound, which is:
 (i) an aliphatic or alicyclic $C_{9-44}$-dicarboxylic acid salt, or
 (ii) an amine of the formula

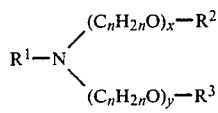

wherein $R^1$ is a $C_{8-22}$ alkyl,
$R^2$ and $R^3$ are, independently, H or $R^4$—COO—, where $R^4$ is a $C_{1-21}$-alkyl or -alkenyl,
n is 2 or 3, and
x and y are, independently, 0 or an integer from 1 to 5, the sum of x+y being in the range 2 to 6.

2. The preparation of claim 1 wherein ingredient:
(C) is liquid at 20° C., and present in an amount of about 5–20% by weight;
(D) has a molecular weight of about 1,000 to 3,000,000, and is present in about 0.5–10% by weight; and
(E) is present in about 5–30% by weight; all weights being based upon the total weight of the preparation.

3. The preparation of claim 1 wherein (C) is a soap derived from at least one linear or branched $C_{12-22}$-fatty acid.

4. The preparation of claim 2 wherein (C) is a soap derived from at least one linear or branched $C_{12-22}$-fatty acid.

5. The preparation of claim 1 wherein (C) is a soap derived from at least one of: oleic, linoleic, palmitoleic, erucic, 2-hexyldecanoic, 2-octyldodecanoic, or isostearic fatty acid.

6. The preparation of claim 2 wherein (C) is a soap derived from at least one of: oleic, linoleic, palmitoleic, erucic, 2-hexyldecanoic, 2-octyldodecanoic, or isostearic fatty acid.

7. The preparation of claim 6 wherein (C) is the reaction product of said at least one fatty acid with an alkali hydroxide, alkali carbonate, ammonia, or mono-, di-, or tri-$C_{2-4}$-alkanolamine.

8. The preparation of claim 1 wherein (C) is the reaction product of oleic acid and ammonia or mono-, di-, or triethanolamine.

9. The preparation of claim 2 wherein (C) is the reaction product of oleic acid and ammonia or mono-, di-, or triethanolamine.

10. The preparation of claim 1 wherein (D) is at least one polymer which contains free or alkyl-substituted amino or quaternary ammonium moieties in the polymer chain.

11. The preparation of claim 2 wherein (D) is at least one polymer which contains free or alkyl-substituted amino or quaternary ammonium moieties in the polymer chain.

12. The preparation of claim 7 wherein (D) is at least one polymer which contains free or alkyl-substituted amino or quaternary ammonium moieties in the polymer chain.

13. The preparation of claim 1 wherein (D) is at least one of:
 (i) a homopolymer or copolymer containing units of the formula

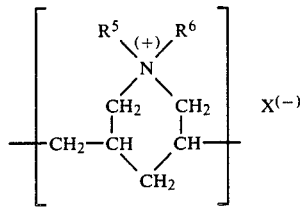

wherein $R^5$ and $R^6$ are, independently, $C_{1-4}$-alkyl or $C_{2-4}$-hydroxyalkyl, and
 $X^{(-)}$ is chloride, bromide, hydrogen sulfate, methosulfate, phosphate, or acetate;
 (ii) a cellulose ether containing anhydroglucose units with 1 to 3 substituents having quaternary ammonium moieties attached by ether linkages; or
 (iii) a quaternary polymeric urea derivative of the formula

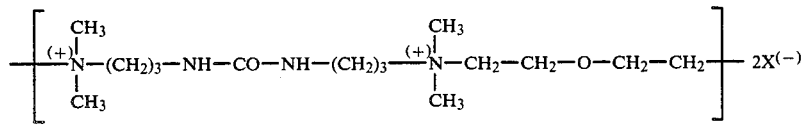

wherein $X^{(-)}$ is as defined above.

14. The preparation of claim 2 wherein (D) is at least one of:
 (i) a homopolymer or copolymer containing units of the formula

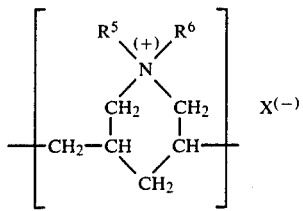

wherein $R^5$ and $R^6$ are, independently, $C_{1-4}$-alkyl or $C_{2-4}$-hydroxyalkyl, and
$X^{(-)}$ is chloride, bromide, hydrogen sulfate, methosulfate, phosphate, or acetate;
(ii) a cellulose ether containing anhydroglucose units with 1 to 3 substituents having quaternary ammonium moeties attached by ether linkages; or
(iii) a quaternary polymeric urea derivative of the formula

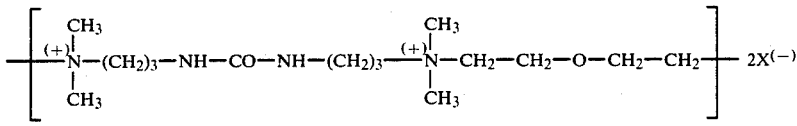

wherein $X^{(-)}$ is as defined above.

15. The preparation of claim 7 wherein (D) is at least one of:

(i) a homopolymer or copolymer containing units of the formula

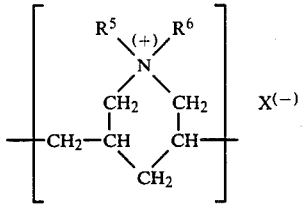

wherein $R^5$ and $R^6$ are, independently, $C_{1-4}$-alkyl or $C_{2-4}$-hydroxyalkyl, and
$X^{(-)}$ is chloride, bromide hydrogen sulfate, methosulfate, phosphate, or acetate;
(ii) a cellulose ether containing anhydroglucose units with 1 to 3 substituents having quaternary ammonium moeties attached by ether linkages; or
(iii) a quaternary polymeric urea derivative of the formula

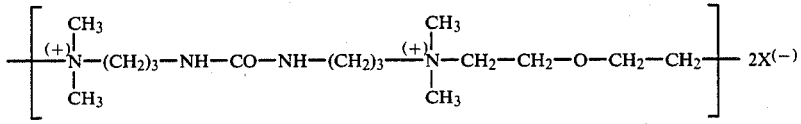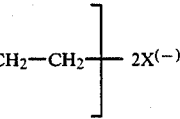

wherein $X^{(-)}$ is as defined above.

16. The preparation of claim 9 wherein (D) is at least one of:

(i) a homopolymer or copolymer containing units of

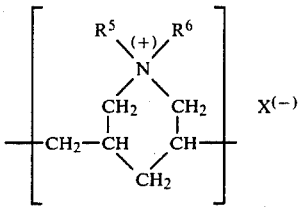

wherein $R^5$ and $R^6$ are, independently, $C_{1-4}$-alkyl or $C_{2-4}$-hydroxyalkyl, and
$X^{(-)}$ is chloride, bromide, hydrogen sulfate, methosulfate, phosphate, or acetate;
(ii) a cellulose ether containing anhydroglucose units with 1 to 3 substituents having quaternary ammonium moieties attached by ether inkages; or
(iii) a quaternary polymeric urea derivative of the formula

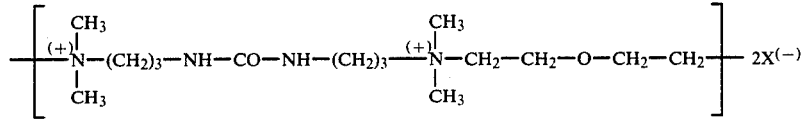

wherein $X^{(-)}$ is as defined above.

17. The preparation of claim 1 wherein (E) is said dicarboxylic acid salt and is at leat one of azelaic acid, sebacic acid, brassylic acid, docosanedioic acid, 2-($C_{5-40}$-alkyl)-succininc acid or anhydride, 2-($C_{5-40}$-alkenyl)-succinic acid or anhydride, dimer acid, or -ene adduct of at least one monounsaturated carboxylic acid with at least one unsaturated fatty acid, in the form of a lithium, sodium, potassium, ammonium, monoethanolammonium, diethanolammonium, triethanolammonium, or isopropanolammonium salt.

18. The preparation of claim 2 wherein (E) is said dicarboxylic acid salt and is at least one of azelaic acid, sebacic acid, brassylic acid, docosanedioic acid, 2-($C_{5-40}$-alkyl)-succinic acid or anhydride, 2-($C_{5-40}$-alkenyl)-succinic acid or anhydride, dimer acid, or -ene adduct of at least one monounsaturated carboxylic acid with at least one unsaturated fatty acid, in the form of a lithium, sodium, potassium, ammonium, monoethanolammonium, diethanolammonium, triethanolammonium, or isopropanolammonium salt.

19. The preparation of claim 7 wherein (E) is said dicarboxylic acid salt and is at least one of azelaic acid, sebacic acid, brassylic acid, docosanedioic acid, 2-($C_{5-40}$-alkyl)-succinic acid or anhydride, 2-($C_{5-40}$-alkenyl)-succinic acid or anhydride, dimer acid, or -ene adduct of at least one monounsaturated carboxylic acid with at least one unsaturated fatty acid, in the form of a lithium, sodium, potassium, ammonium, monoethanolammonium, diethanolammonium, triethanolammonium, or isopropanolammonium salt.

20. The preparation of claim 9 wherein (E) is said dicarboxylic acid salt and is at least one of azelaic acid, sebacic acid, brassylic acid, docosanedioic acid, 2-($C_{5-40}$-alkyl)-succinic acid or anhydride, 2-($C_{5-40}$-alkenyl)-succinic acid or anhydride, dimer acid, or -ene adduct of at least one monounsaturated carboxylic acid with at least one unsaturated fatty acid, in the form of a lithium, sodium, potassium, ammonium, monoethanolammonium, diethanolammonium, triethanolammonium, or isopropanolammonium salt.

21. The preparation of claim 11 wherein (E) is said dicarboxylic acid salt and is at least one of azelaic acid, sebacic acid, brassylic acid, docosanedioic acid, 2-($C_{5-40}$-alkyl)-succinic acid or anhydride, 2-($C_{5-40}$-alkenyl)-succinic acid or anhydride, dimer acid, or -ene adduct of at least one monounsaturated carboxylic acid with at least one unsaturated fatty acid, in the form of a lithium, sodium, potassium, ammonium, monoethanolammonium, diethanolammonium, triethanolammonium, or isopropanolammonium salt.

22. The preparation of claim 12 wherein (E) is said dicarboxylic acid salt and is at least one of azelaic acid, sebacic acid, brassylic acid, docosanedioic acid, 2-($C_{5-40}$-alkyl)-succinic acid or anhydride, 2-($C_{5-40}$-alkenyl)-succinic acid or anhydride, dimer acid, or -ene adduct of at least one monounsaturated carboxylic acid with at least one unsaturated fatty acid, in the form of a lithium, sodium, potassium, ammonium, monoethanolammonium, diethanolammonium, triethanolammonium, or isopropanolammonium salt.

23. The preparation of claim 1, 2, 7, 9, 11 or 12, wherein ingredient (E) is at least a salt of 5(6)-carboxy-4-hexyl-2-cyclohexane-1-octanoic acid.

24. The preparation of claim 17, 18, 19, 20, 21, or 22, consisting essentially of the stated ingredients plus a $C_{1-4}$-alcohol, $C_{2-6}$ glycol, or any mixture thereof, present in about 10–30% by weight, and 0 to about 20% by weight of at least one $C_{12-22}$ fatty alcohol.

25. The preparation of claim 23 consisting essentially of the stated ingredients plus a $C_{1-4}$-alcohol, $C_{2-6}$ glycol, or any mixture thereof, present in about 10–30% by weight, and 0 to about 20% by weight of at least one $C_{12-22}$ fatty alcohol.

26. A method for stabilizing a hair dye preparation comprising ingredients (A), (B), (C), and (D) of claim 17, 18, 19, 20, 21, or 22, comprising adding a compound consisting essentially of ingredient (E).

27. A method of dyeing hair comprising applying to said hair, for a hair dyeing effective time, and in a hair dyeing effective amount, the preparation according to claim 1, 2, 7 or 14 in combination with an aqueous oxidizing developer.

28. A method for dyeing hair comprising applying to said hair, for a hair dyeing effective time, and in a hair dyeing effective amount, the preparation according to claim 24 in combination with an aqueous oxidizing developer.

* * * * *